(12) United States Patent
Jimenez et al.

(10) Patent No.: US 8,940,049 B1
(45) Date of Patent: Jan. 27, 2015

(54) EXPANDABLE INTERVERTEBRAL CAGE

(71) Applicant: Ex Technology, LLC, Gering, NE (US)

(72) Inventors: Omar F. Jimenez, Gering, NE (US); Yefim Safris, Golden Valley, MN (US)

(73) Assignee: Ex Technology, LLC, Gering, NE (US)

(*) Notice: Subject to any disclaimer, the term of this patent is extended or adjusted under 35 U.S.C. 154(b) by 0 days.

(21) Appl. No.: 14/242,451

(22) Filed: Apr. 1, 2014

(51) Int. Cl.
*A61F 2/44* (2006.01)

(52) U.S. Cl.
CPC ........................................ *A61F 2/447* (2013.01)
USPC ..................................................... 623/17.15

(58) Field of Classification Search
CPC ........... A61F 2/442; A61F 2002/30579; A61F 2002/30471; A61F 2002/30411
USPC .......................................... 623/17.11–17.16
See application file for complete search history.

(56) References Cited

U.S. PATENT DOCUMENTS

| | | | |
|---|---|---|---|
| 2,106,088 A | 1/1938 | De Tar |
| 2,231,221 A | 2/1941 | Rector |
| 2,453,656 A | 11/1948 | Bullard, III |
| 2,666,334 A | 1/1954 | Nalle |
| 2,711,105 A | 6/1955 | Williams |
| 2,842,976 A | 7/1958 | Young |
| 2,891,408 A | 6/1959 | Burt, Jr. |
| 3,386,128 A | 6/1968 | Vyvyan |
| 3,449,971 A | 6/1969 | Posh |
| 3,575,475 A | 4/1971 | Boerner |
| 3,596,863 A | 8/1971 | Kaspareck |
| 3,597,938 A | 8/1971 | Hellen |
| 3,700,289 A | 10/1972 | Bilinski et al. |
| 3,700,290 A | 10/1972 | Ensinger |
| 3,708,925 A | 1/1973 | Ainoura |
| 3,709,132 A | 1/1973 | Farrell et al. |
| 3,916,596 A | 11/1975 | Hawley |
| 3,985,000 A | 10/1976 | Hartz |
| 3,988,906 A | 11/1976 | Smith |
| 4,261,211 A | 4/1981 | Haberland |

(Continued)

FOREIGN PATENT DOCUMENTS

| | | |
|---|---|---|
| EP | 1342456 A1 | 9/2003 |
| EP | 1552797 A2 | 7/2005 |

(Continued)

OTHER PUBLICATIONS

PCT/US2010/042941, filed Jul. 22, 2010, International Search Report and Written Opinion, dated Apr. 25, 2011.

(Continued)

*Primary Examiner* — Ellen C Hammond
*Assistant Examiner* — Jacqueline Johanas
(74) *Attorney, Agent, or Firm* — Patterson Thuente Pedersen, P.A.

(57) ABSTRACT

An expandable intervertebral cage adapted to be implanted into an intervertebral disc space in a patient's body, the expandable intervertebral cage including first and second base plates having outer surfaces configured to interface with vertebra in the intervertebral disc space, a first, second and third arm assembly hingedly connected to first and second base plates, and first and second actuation members, wherein rotation of the first actuation member pulls the second arm assembly towards the first arm assembly and rotation of the second actuation member pulls the third arm assembly towards the second arm assembly, the first actuation member and the second actuation member capable of being actuated independently of each other.

18 Claims, 10 Drawing Sheets

(56) References Cited

U.S. PATENT DOCUMENTS

| | | | |
|---|---|---|---|
| 4,396,047 A | 8/1983 | Balkus | |
| 4,478,109 A | 10/1984 | Kobelt | |
| 4,516,303 A | 5/1985 | Kloster | |
| 4,528,864 A | 7/1985 | Craig | |
| 4,559,717 A | 12/1985 | Scire et al. | |
| 4,630,495 A | 12/1986 | Smith | |
| 4,691,586 A | 9/1987 | van Leijenhorst et al. | |
| 4,694,703 A | 9/1987 | Routson | |
| 4,869,552 A | 9/1989 | Tolleson et al. | |
| 5,133,108 A | 7/1992 | Esnault | |
| 5,181,371 A | 1/1993 | Deworth | |
| 5,196,857 A | 3/1993 | Chiappetta et al. | |
| 5,198,932 A | 3/1993 | Takamura | |
| 5,222,986 A | 6/1993 | Wright | |
| 5,313,852 A | 5/1994 | Arena | |
| 5,374,556 A | 12/1994 | Bennett et al. | |
| 5,439,377 A | 8/1995 | Milanovich | |
| 5,445,471 A | 8/1995 | Wexler et al. | |
| 5,645,599 A | 7/1997 | Samani | |
| 5,664,457 A | 9/1997 | Nejati | |
| 5,904,479 A | 5/1999 | Staples | |
| 5,960,670 A | 10/1999 | Iverson et al. | |
| 5,980,252 A | 11/1999 | Samchukov et al. | |
| 5,988,006 A | 11/1999 | Fleytman | |
| 6,045,579 A | 4/2000 | Hochshuler et al. | |
| 6,056,491 A | 5/2000 | Hsu | |
| 6,136,031 A | 10/2000 | Middleton | |
| 6,175,989 B1 | 1/2001 | Carpenter et al. | |
| 6,315,797 B1 | 11/2001 | Middleton | |
| 6,350,317 B1 | 2/2002 | Hao et al. | |
| 6,378,172 B1 | 4/2002 | Schrage | |
| 6,395,035 B2 | 5/2002 | Bresina et al. | |
| 6,454,806 B1 | 9/2002 | Cohen et al. | |
| 6,484,608 B1 | 11/2002 | Ziavras | |
| 6,517,772 B1 | 2/2003 | Woolf | |
| 6,554,526 B1 | 4/2003 | Egelandsdal | |
| 6,616,695 B1 | 9/2003 | Crozet et al. | |
| 6,641,614 B1 * | 11/2003 | Wagner et al. | 623/17.15 |
| 6,719,796 B2 * | 4/2004 | Cohen et al. | 623/17.15 |
| 6,752,832 B2 | 6/2004 | Neumann | |
| 6,772,479 B2 | 8/2004 | Hinkley et al. | |
| 6,802,229 B1 | 10/2004 | Lambert | |
| 6,808,537 B2 | 10/2004 | Michelson | |
| 6,863,673 B2 | 3/2005 | Gerbec et al. | |
| 6,932,844 B2 | 8/2005 | Ralph et al. | |
| 6,953,477 B2 | 10/2005 | Berry | |
| 7,018,415 B1 | 3/2006 | McKay | |
| 7,051,610 B2 | 5/2006 | Stoianovici et al. | |
| 7,070,598 B2 * | 7/2006 | Lim et al. | 606/99 |
| 7,087,055 B2 * | 8/2006 | Lim et al. | 606/99 |
| 7,201,751 B2 | 4/2007 | Zucherman et al. | |
| 7,273,373 B2 | 9/2007 | Horiuchi | |
| 7,308,747 B2 | 12/2007 | Smith et al. | |
| 7,316,381 B2 | 1/2008 | Häcker et al. | |
| 7,410,201 B1 | 8/2008 | Wilson et al. | |
| 7,425,103 B2 | 9/2008 | Perez-Sanchez | |
| 7,435,032 B1 | 10/2008 | Murphey et al. | |
| 7,547,325 B2 * | 6/2009 | Biedermann et al. | 623/17.16 |
| 7,584,682 B2 | 9/2009 | Hsiao | |
| 7,611,538 B2 | 11/2009 | Belliard et al. | |
| 7,632,281 B2 | 12/2009 | Errico et al. | |
| 7,674,296 B2 | 3/2010 | Rhoda et al. | |
| 7,682,376 B2 | 3/2010 | Trieu | |
| 7,708,779 B2 | 5/2010 | Edie et al. | |
| 7,712,389 B2 | 5/2010 | Wang | |
| 7,753,958 B2 | 7/2010 | Gordon et al. | |
| 7,758,645 B2 | 7/2010 | Studer | |
| 7,758,648 B2 | 7/2010 | Castleman et al. | |
| 7,892,285 B2 | 2/2011 | Viker | |
| 7,896,919 B2 | 3/2011 | Belliard et al. | |
| 7,947,078 B2 | 5/2011 | Siegal | |
| 7,985,256 B2 | 7/2011 | Grotz et al. | |
| 8,070,813 B2 | 12/2011 | Grotz et al. | |
| 8,192,495 B2 | 6/2012 | Simpson et al. | |
| 8,303,663 B2 | 11/2012 | Jimenez et al. | |
| 8,523,944 B2 * | 9/2013 | Jimenez et al. | 623/17.15 |
| 8,628,577 B1 * | 1/2014 | Jimenez | 623/17.15 |
| 8,771,360 B2 | 7/2014 | Jimenez et al. | |
| 2002/0128716 A1 * | 9/2002 | Cohen et al. | 623/17.15 |
| 2003/0077110 A1 | 4/2003 | Knowles | |
| 2003/0233145 A1 | 12/2003 | Landry et al. | |
| 2004/0049271 A1 * | 3/2004 | Biedermann et al. | 623/17.11 |
| 2004/0111157 A1 | 6/2004 | Ralph et al. | |
| 2004/0153156 A1 * | 8/2004 | Cohen et al. | 623/17.13 |
| 2004/0225364 A1 | 11/2004 | Richelsoph et al. | |
| 2005/0000228 A1 | 1/2005 | De Sousa et al. | |
| 2005/0033431 A1 | 2/2005 | Gordon et al. | |
| 2005/0095384 A1 | 5/2005 | Wittmeyer | |
| 2005/0113921 A1 | 5/2005 | An et al. | |
| 2005/0113924 A1 | 5/2005 | Buttermann | |
| 2005/0175406 A1 | 8/2005 | Perez-Sanchez | |
| 2005/0261769 A1 * | 11/2005 | Moskowitz et al. | 623/17.11 |
| 2006/0004447 A1 | 1/2006 | Mastrorio et al. | |
| 2006/0004455 A1 | 1/2006 | Leonard et al. | |
| 2006/0025862 A1 | 2/2006 | Villiers et al. | |
| 2006/0129244 A1 | 6/2006 | Ensign | |
| 2006/0149385 A1 | 7/2006 | McKay | |
| 2006/0184171 A1 | 8/2006 | Biedermann et al. | |
| 2006/0247781 A1 | 11/2006 | Francis | |
| 2006/0293752 A1 | 12/2006 | Moumene et al. | |
| 2007/0032791 A1 | 2/2007 | Greenhalgh et al. | |
| 2007/0049943 A1 | 3/2007 | Moskowitz et al. | |
| 2007/0083267 A1 | 4/2007 | Miz et al. | |
| 2007/0129730 A1 | 6/2007 | Woods et al. | |
| 2007/0185577 A1 | 8/2007 | Malek | |
| 2007/0191954 A1 | 8/2007 | Hansell et al. | |
| 2007/0191958 A1 | 8/2007 | Abdou | |
| 2007/0198089 A1 | 8/2007 | Moskowitz et al. | |
| 2007/0219634 A1 | 9/2007 | Greenhalgh et al. | |
| 2007/0222100 A1 | 9/2007 | Husted et al. | |
| 2007/0255415 A1 | 11/2007 | Edie et al. | |
| 2007/0282449 A1 | 12/2007 | de Villiers et al. | |
| 2007/0293329 A1 | 12/2007 | Glimpel et al. | |
| 2007/0293948 A1 | 12/2007 | Bagga et al. | |
| 2008/0026903 A1 | 1/2008 | Flugrad et al. | |
| 2008/0077246 A1 | 3/2008 | Fehling et al. | |
| 2008/0091211 A1 | 4/2008 | Gately | |
| 2008/0100179 A1 | 5/2008 | Ruggeri et al. | |
| 2008/0103601 A1 * | 5/2008 | Biro et al. | 623/17.16 |
| 2008/0114367 A1 * | 5/2008 | Meyer | 606/90 |
| 2008/0140207 A1 | 6/2008 | Olmos | |
| 2008/0147194 A1 | 6/2008 | Grotz et al. | |
| 2008/0161920 A1 | 7/2008 | Melkent | |
| 2008/0161931 A1 | 7/2008 | Perez-Cruet et al. | |
| 2008/0168855 A1 | 7/2008 | Giefer et al. | |
| 2008/0183204 A1 * | 7/2008 | Greenhalgh et al. | 606/198 |
| 2008/0188941 A1 | 8/2008 | Grotz | |
| 2008/0210039 A1 | 9/2008 | Brun | |
| 2008/0221694 A1 | 9/2008 | Warnick et al. | |
| 2008/0234736 A1 | 9/2008 | Trieu et al. | |
| 2008/0281423 A1 | 11/2008 | Sheffer et al. | |
| 2008/0292392 A1 | 11/2008 | Voellmer | |
| 2008/0319487 A1 | 12/2008 | Fielding et al. | |
| 2009/0012564 A1 | 1/2009 | Chirico et al. | |
| 2009/0076614 A1 | 3/2009 | Arramon | |
| 2009/0164017 A1 | 6/2009 | Sommerich et al. | |
| 2009/0210061 A1 | 8/2009 | Sledge | |
| 2009/0222100 A1 | 9/2009 | Cipoletti et al. | |
| 2010/0004688 A1 | 1/2010 | Maas et al. | |
| 2010/0082109 A1 | 4/2010 | Greenhalgh et al. | |
| 2010/0094305 A1 | 4/2010 | Chang et al. | |
| 2010/0185291 A1 * | 7/2010 | Jimenez et al. | 623/17.16 |
| 2010/0192715 A1 | 8/2010 | Vauchel et al. | |
| 2010/0209184 A1 | 8/2010 | Jimenez et al. | |
| 2011/0015638 A1 * | 1/2011 | Pischl et al. | 606/90 |
| 2011/0054616 A1 | 3/2011 | Kamran et al. | |
| 2011/0093075 A1 | 4/2011 | Duplessis et al. | |
| 2011/0112644 A1 | 5/2011 | Zilberstein et al. | |
| 2011/0138948 A1 | 6/2011 | Jimenez et al. | |
| 2011/0160861 A1 | 6/2011 | Jimenez et al. | |
| 2011/0270398 A1 | 11/2011 | Grotz et al. | |
| 2012/0116518 A1 | 5/2012 | Grotz et al. | |
| 2012/0158071 A1 | 6/2012 | Jimenez et al. | |
| 2012/0323329 A1 | 12/2012 | Jimenez et al. | |

(56) References Cited

U.S. PATENT DOCUMENTS

| | | |
|---|---|---|
| 2013/0053966 A1 | 2/2013 | Jimenez et al. |
| 2013/0144388 A1* | 6/2013 | Emery et al. .............. 623/17.16 |
| 2013/0197642 A1* | 8/2013 | Ernst ........................ 623/17.16 |
| 2013/0317615 A1* | 11/2013 | Jimenez et al. ............ 623/17.15 |
| 2014/0012383 A1* | 1/2014 | Triplett et al. ............. 623/17.16 |
| 2014/0039622 A1* | 2/2014 | Glerum et al. ............. 623/17.15 |
| 2014/0194991 A1* | 7/2014 | Jimenez ..................... 623/17.15 |

FOREIGN PATENT DOCUMENTS

| | | |
|---|---|---|
| EP | 1881209 A1 | 1/2008 |
| JP | 05-81194 | 4/1993 |
| JP | 2004-301135 A | 10/2004 |
| JP | 2008-208932 A | 9/2008 |
| WO | WO 2004/026188 A2 | 4/2004 |
| WO | WO 2004/109155 A1 | 12/2004 |
| WO | WO 2005/081330 A2 | 9/2005 |
| WO | WO 2005/096975 A2 | 10/2005 |
| WO | WO 2006/094535 A1 | 9/2006 |
| WO | WO 2006/116052 A2 | 11/2006 |
| WO | WO 2006/125329 A1 | 11/2006 |
| WO | WO 2007/002583 A2 | 1/2007 |
| WO | WO 2007/009107 A2 | 1/2007 |
| WO | WO 2007/028140 A2 | 3/2007 |
| WO | WO 2007/076377 A2 | 7/2007 |
| WO | WO 2007/111979 A2 | 10/2007 |
| WO | WO 2008/137192 A1 | 11/2008 |
| WO | WO 2009/018349 A2 | 2/2009 |
| WO | WO 2010/078520 A2 | 7/2010 |

OTHER PUBLICATIONS

PCT/US2010/042915, filed Jul. 22, 2010, Search Report dated Apr. 22, 2011.

PCT/US2009/069876, filed Dec. 30, 2009, International Search Report and Written Opinion dated Sep. 27, 2010, 12 pages.

PCT/US2009/069958, filed Dec. 31, 2009, International Search Report and Written Opinion dated Nov. 29, 2010, 9 pages.

European Application No. EP 09837185, European Search Report dated May 14, 2013, 7 pages.

PCT/US2009/069958, filed Dec. 31, 2009, Transmittal of IPRP dated Jul. 14, 2011, 4 pages.

Wenzel Spine, Inc., VariLift®-L Expandable Interbody Fusion Device: A proven solution for stand-alone fusion, Product Overview, 12 pages, 2010.

Peter A. Halverson, et. al., Tension-based Multi-stable Compliant: Rolling-contact Elements, Department of Mechanical Engineering, Brigham Young University, Provo UT, USA 84602, 34 pages, 2007.

Just L. Herder, Force Directed Design of Laparoscopic Forceps, ASME Design Engineering Technical Conference, 8 pages, 1998.

Alexander H. Slocum, Fundamentals of Design, 2005.

W. Küsswetter, A Supplementary Instrumentation for Posterior Fusion of Spine in Scoliosis, Archives of Orthopedic Traumatic Surgery, 1980, 1 page.

Chou et al., Efficacy of Anterior Cervical Fusion: Comparison of Titanium Cages, polyetheretherketone (PEEK) cages and autogenous bone grafts, Journal of Clinical Neuroscience, 2008, pp. 1240-1245.

Amelie Jeanneau, et. al., A Compliant Rolling Contact Joint and its Application in a 3-DOF Planar Parallel Mechanism with Kinematic Analysis, ASME, Design Engineering Technical Conferences, 9 pages, 2004.

Hunter et al., Overview of Medical Devices, Department of Radiology, University of Arizona, Aug. 2001, pp. 89-140, vol. 30, No. 4, ISSN: 0363-0188.

Medtronic Sofamor Danek USA, Inc., *CAPSTONE* Instrument Set Technique, http://www.mtortho.com/public/capstone.pdf , © 2005, 25 pages.

Medtronic, Capstone Peek Spinal System Surgical Technique, http://www.mtortho.com/public/capstone_peek_st.pdf, © 2009, 36 pages.

Application and File History for U.S. Appl. No. 12/651,266, filed Dec. 31, 2009, Inventors Jimenez et al.

Application and File History for U.S. Appl. No. 12/841,465, filed Jul. 22, 2010, now U.S. Patent No. 8,303,663, Inventors Jimenez et al.

Application and File History for U.S. Appl. No. 12/841,869, filed Jul. 22, 2010, Inventors Jimenez et al.

Application and File History for U.S. Appl. No. 13/189,410, filed Jul. 22, 2011, Inventor Jimenez.

Application and File History for U.S. Appl. No. 13/661,534, filed Oct. 26, 2012, Inventor Jimenez.

Application and File History for U.S. Appl. No. 14/024,764, filed Sep. 12, 2013, Inventor Jimenez et al.

Application and File history for U.S. Appl. No. 12/407,608, filed Mar. 19, 2009, now U.S. Patent No. 8,628,577, issued Jan. 14, 2014. Inventors: Jimenez.

Application and File history for U.S. Appl. No. 12/650,994, filed Dec. 31, 2009, now U.S. Patent No. 8,523,944, issued Sep. 3, 2013. Inventors: Jimenez et al.

Application and File history for U.S. Appl. No. 13/591,463, filed Aug. 22, 2012, now U.S. Patent No. 8,771,360, issued Jul. 8, 2014. Inventors: Jimenez et al.

Application and File history for U.S. Appl. No. 13/891,356, filed May 10, 2013. Inventors: Jimenez et al.

Application and File history for U.S. Appl. No. 14/153,281, filed Jan. 13, 2014. Inventors: Jimenez.

* cited by examiner

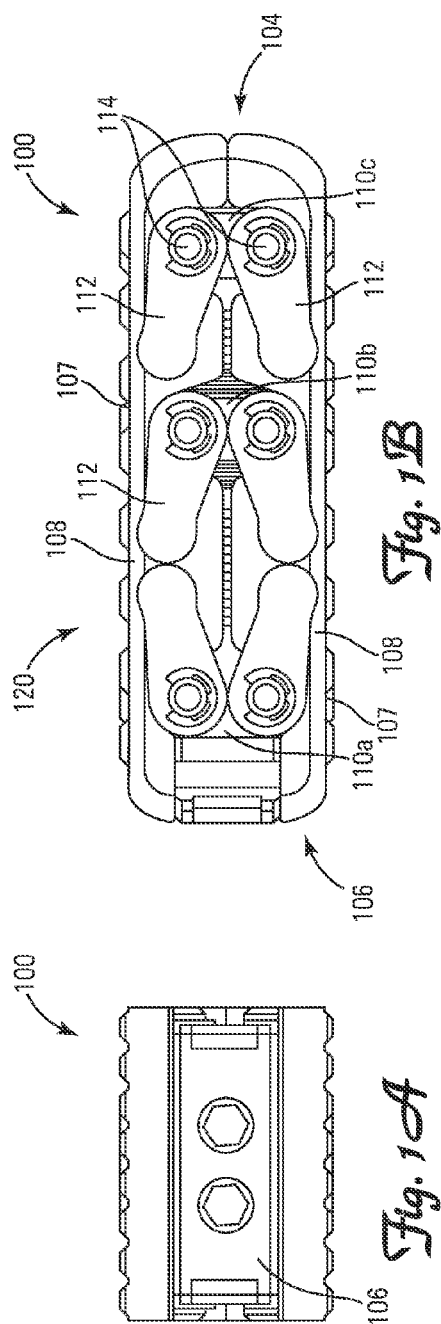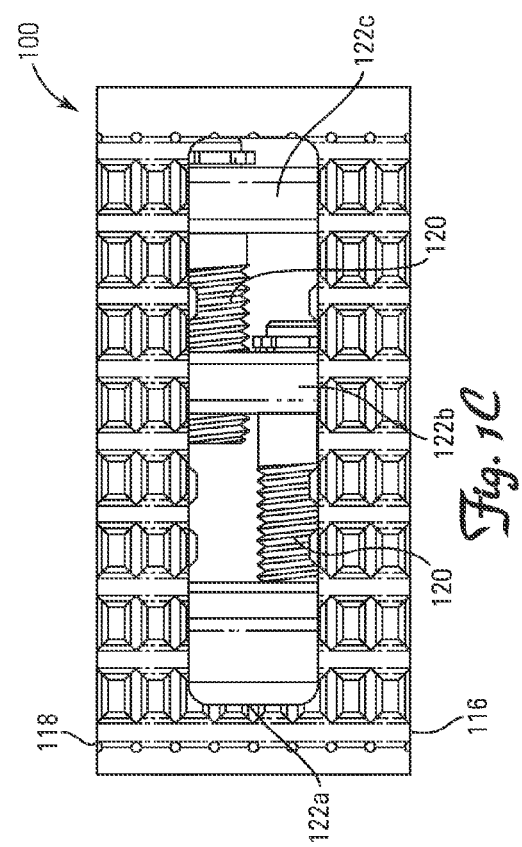

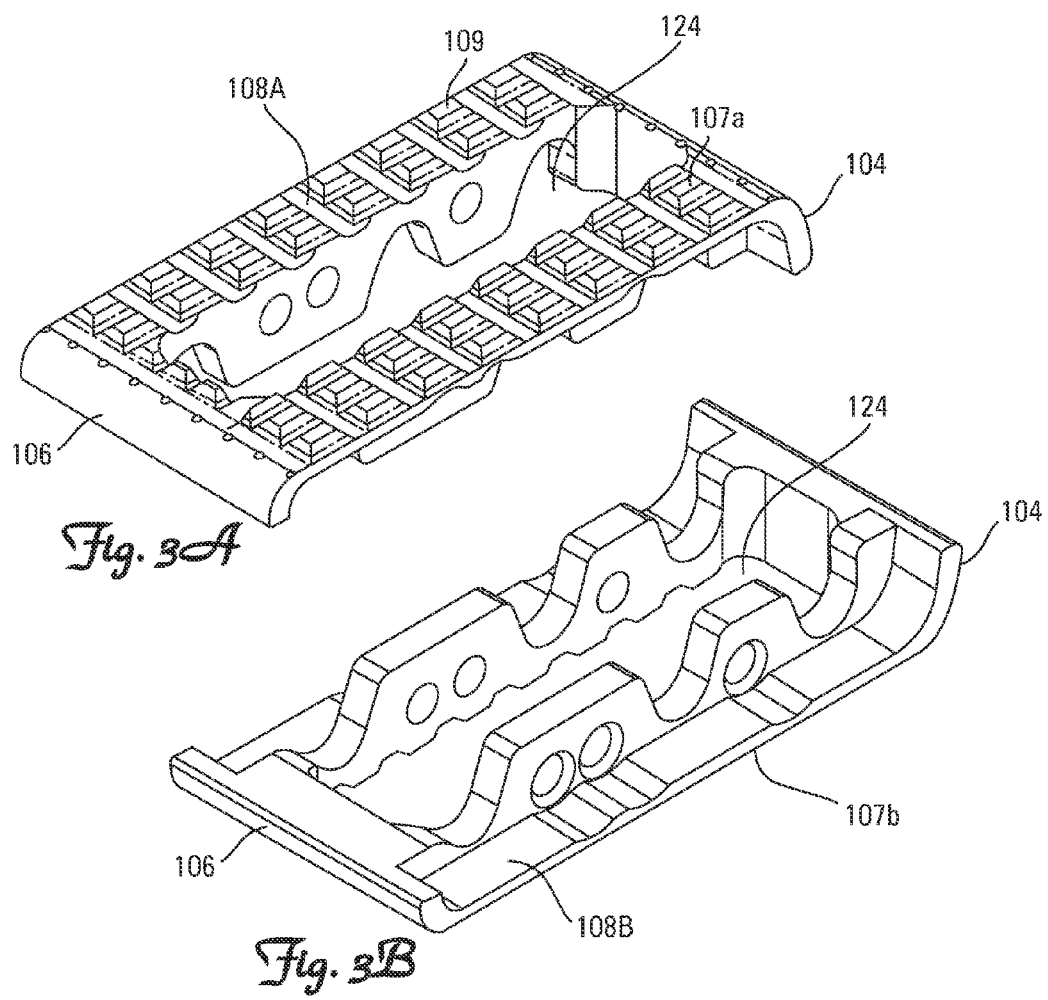
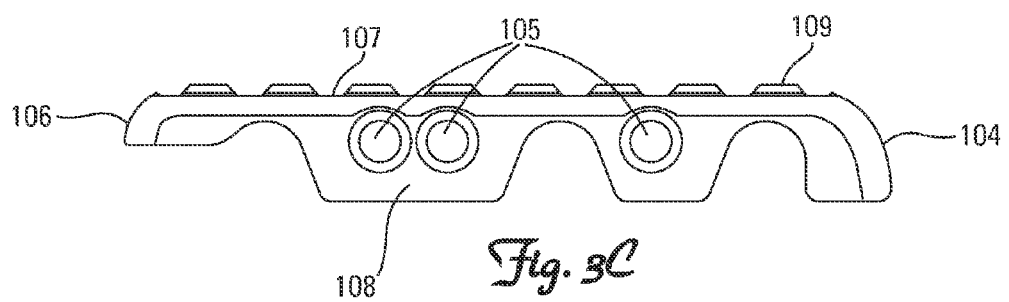

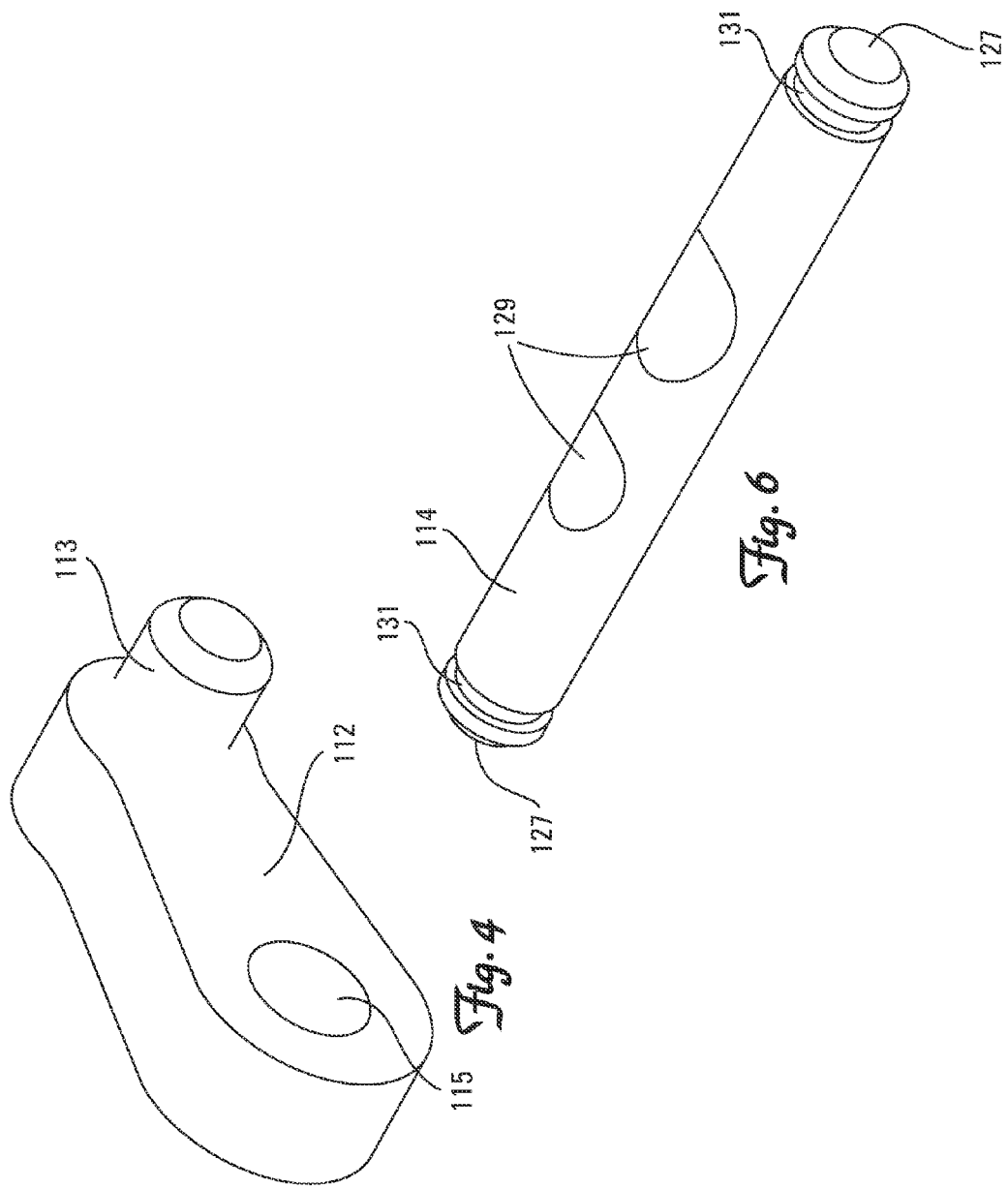

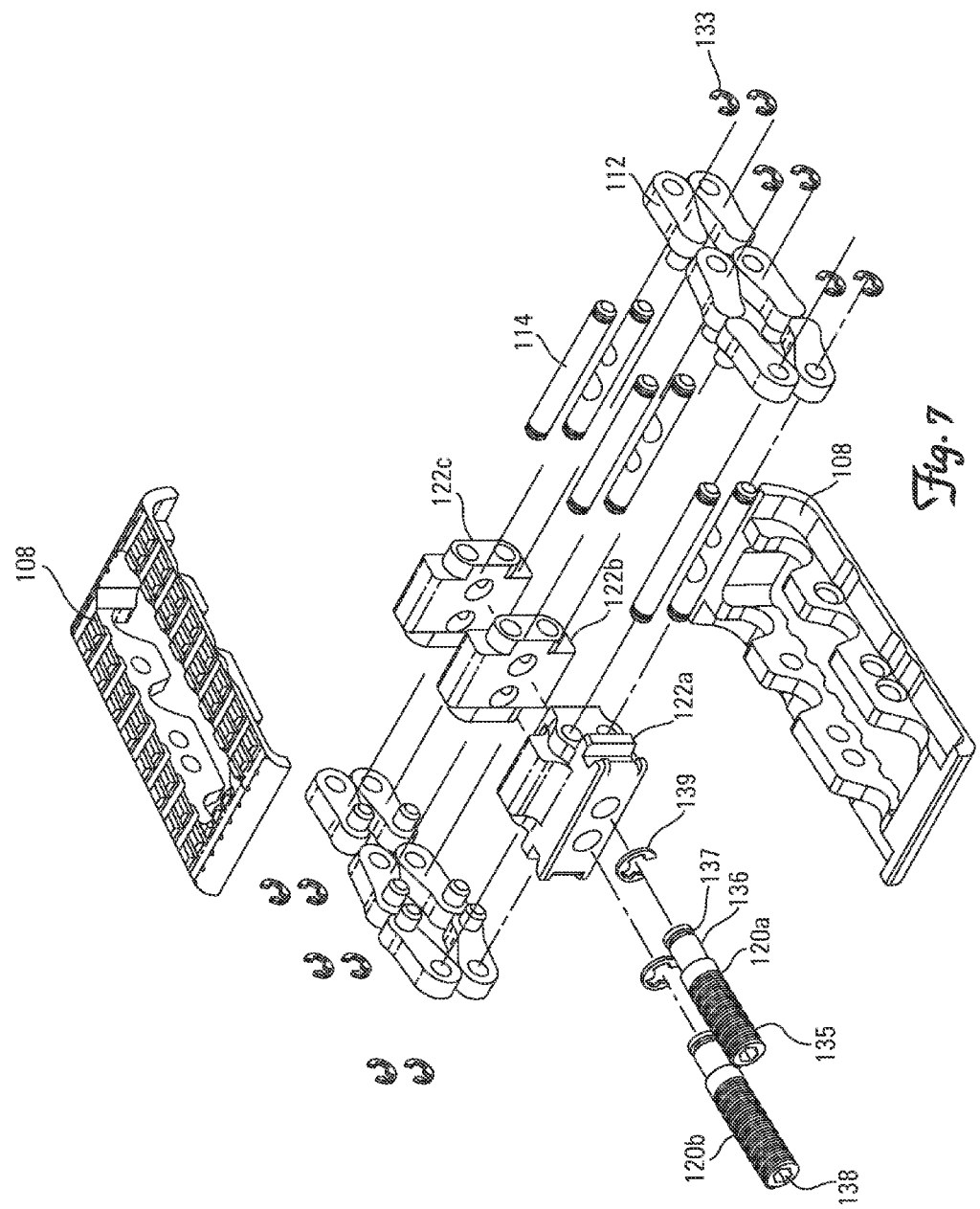

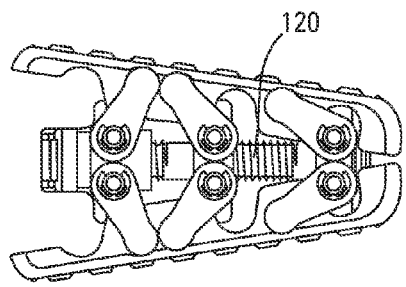
Fig. 8A
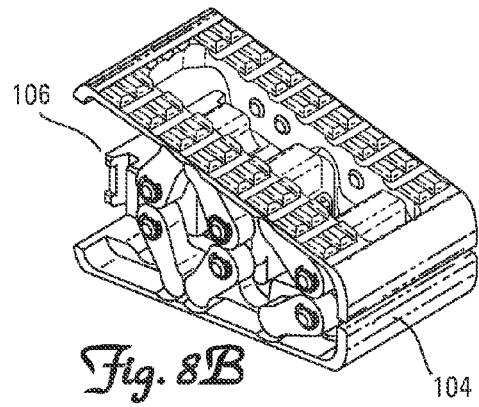
Fig. 8B
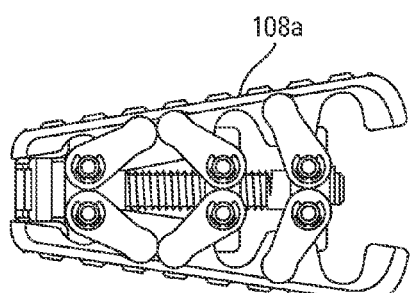
Fig. 9A
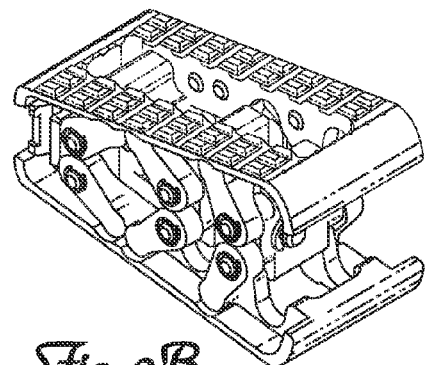
Fig. 9B
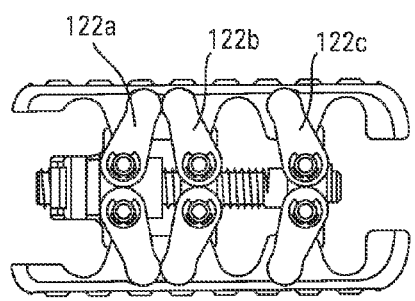
Fig. 10-A
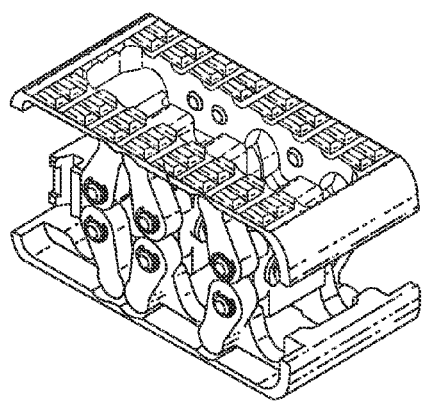
Fig. 10B

EXPANDABLE INTERVERTEBRAL CAGE

TECHNICAL FIELD

The present invention relates to the distraction and fusion of vertebral bodies. More specifically, the present invention relates to devices and associated methods for distraction and fusion of vertebral bodies that remain stable when implanted and facilitate fusion following their use for distraction to aid in the correction of spinal deformity by reducing a collapsed disc and establishing sagittal alignment, lordosis, or kyphosis.

BACKGROUND

The concept of intervertebral fusion for the cervical and lumbar spine following a discectomy was generally introduced in the 1960s. It involved coring out a bone graft from the hip and implanting the graft into the disc space. The disc space was prepared by coring out the space to match the implant. The advantages of this concept were that it provided a large surface area of bone to bone contact and placed the graft under loading forces that allowed osteoconduction and induction enhancing bone fusion. However, the technique is seldom practiced today due to numerous disadvantages including lengthy operation time, destruction of a large portion of the disc space, high risk of nerve injury, and hip pain after harvesting the bone graft.

Presently, at least two devices are commonly used to perform the intervertebral portion of an intervertebral body fusion: the first is the distraction device and the second is the intervertebral body fusion device, often referred to as a cage. Cages can be implanted as standalone devices or as part of a circumferential fusion approach with pedicle screws and rods. The concept is to introduce an implant that will distract a collapsed disc and decompress the nerve root, allow load sharing to enhance bone formation and to implant a device that is small enough to allow implantation with minimal retraction and pulling on nerves.

In a typical intervertebral body fusion procedure, a portion of the intervertebral disc is first removed from between the vertebral bodies. This can be done through either a direct open approach or a minimally invasive approach. Disc shavers, pituitary rongeours, curettes, and/or disc scrapers can be used to remove the nucleus and a portion of either the anterior or posterior annulus to allow implantation and access to the inner disc space. The distraction device is inserted into the cleared space to enlarge the disc space and the vertebral bodies are separated by actuating the distraction device. Enlarging the disc space is important because it also opens the foramen where the nerve root exists. It is important that during the distraction process one does not over-distract the facet joints. An intervertebral fusion device is next inserted into the distracted space and bone growth factor, such as autograft, a collagen sponge with bone morphogenetic protein, or other bone enhancing substance may be inserted into the space within the intervertebral fusion device to promote the fusion of the vertebral bodies.

Intervertebral fusion and distraction can be performed through anterior, posterior, oblique, and lateral approaches. Each approach has its own anatomical challenges, but the general concept is to fuse adjacent vertebra in the cervical thoracic or lumbar spine. Devices have been made from various materials. Such materials include cadaveric cancellous bone, carbon fiber, titanium and polyetheretherketone (PEEK). Devices have also been made into different shapes such as a bean shape, football shape, banana shape, wedge shape and a threaded cylindrical cage.

U.S. Pat. Nos. 7,070,598 and 7,087,055 to Lim et al. disclose minimally invasive devices for distracting the disc space. The devices include scissor-jack-like linkages that are used to distract a pair of endplates associated with adjacent vertebra from a first collapsed orientation to a second expanded orientation. A pull arm device is used to deliver and distract the device in the disc space. However, the device is primarily used for distraction and not subsequent vertebral fusion. The device would not work as a fusion device, because once the pull arm is disconnected from the device, the device will not be stable enough to maintain proper spacing of the vertebrae until fusion can occur. The endplates of the device are also solid and do not permit bone growth for successful fusion.

U.S. Patent Publication No. 2008/0114367 to Meyer discloses a device that uses a scissor-jack-like arrangement to distract a disc space. To solve the instability problem of the scissor-jack arrangement, a curable polymer is injected to fill the disc space and the distraction device is disabled from attempting to support the load. The curable polymer and disabling of the device are necessary because the device could not adequately support the distracted disc space. The base plates of the device have at least two or more degrees of freedom, collectively, in a distracted position and are therefore not stable under the loads encountered supporting the disc space. Absent injection of the polymer, and the support and control supplied by the implanting physician via the removable distraction tool, the base plates would collapse, which could cause severe damage to the vertebral bodies.

Accordingly, there is a need in the art for a device that can distract adjacent vertebral bodies in a minimally invasive manner while providing stable support for the disc space during fusion; particularly, a device that would allow for angular orientation of the base plates to be matched exactly to the unique alignment, or desired alignment, of a patient's spine.

SUMMARY OF THE DISCLOSURE

Improved methods and apparatuses for vertebral body distraction and fusion in accordance with various embodiments of the present invention employ a device that can stay in the body of a patient and stably support the disc space during vertebral fusion following its use as a distraction device. Moreover, various embodiments of the present invention are configurable in a manner allowing angular orientation of the base plates to be matched more precisely to the unique planar alignment, or desired alignment, of adjacent vertebrae of a patient's spine.

In one embodiment, a device can be used for both intervertebral distraction and fusion of an intervertebral disc space. The device can include a first top base plate having a first outer bearing surface configured to interface with a first vertebra of the intervertebral disc space, for example, an end plate of a superior vertebra of the intervertebral disc space, and a second bottom base plate having a second outer bearing surface configured to interface with a second vertebra of the intervertebral disc space, for example an inferior vertebra of the intervertebral disc space. First, second and third arm assemblies can be hinged and connected to the first base plate and the second base plate. In some embodiments, each arm assembly can include a block and a pair of opposing arms. A first threaded actuation member can extend through the first arm assembly and into the second arm assembly, while a second threaded actuation member can extend through the second arm assembly and into the third arm assembly. The actuation members can be configured such that actuation of the first actuation member causes expansion of the first and second arm assemblies, and actuation of the second actuation member causes expansion of the second and third arm assemblies. The first actuation member and the second actuation member can be capable of being actuated independently of each other thereby angling the base plates to enable the angular orientation of the first and second base plates to be matched more precisely to the unique planar alignment, or desired alignment, of adjacent vertebrae of a patient's spine.

The device is designed to be capable of supporting prolonged, compressive loading of greater than 2000-3000 [N]; oblique shear loading of greater than 1200-1500 [N]; and torsion of greater than 10-20 [N]. The device is configured to be inserted into the disc space and distracted from a compressed configuration to an expanded configuration to distract the disc space. Mechanisms for stabilizing that constrain the device to zero, or fewer, degrees of freedom of movement enable the device to stably support the disc space. A bone growth stimulant for promoting vertebral fusion can be inserted into an open space defined by the device, which continues to stably support the disc space during vertebral fusion.

Optionally, some flexibility or compliance can be built into the device, while maintaining the stability of the device, by selecting flexible materials for some of the rigid members/arms and or by manipulating the fits of the numerous joints. Flexible material may also be added to, in, around, or between elements of the device to additionally support flexibility, while maintaining, or in some embodiments, enhancing, the stability of the device by reducing potential hysteresis.

In another embodiment, a method of intervertebral body distraction and fusion involves implantation of a distractible intervertebral body fusion device into an intervertebral disc space. The device is inserted such that a top bearing surface of a top base plate of the device interfaces with an end plate of a superior vertebra of the disc space and a bottom bearing surface of a bottom base plate interfaces with an end plate of an inferior vertebra of the disc space. The device is distracted into an expanded configuration such that the top base plate and bottom base plate are vertically separated from each other to expand the disc space. A bone growth promoting material can then be inserted into the disc space into an open space defined by the device to encourage bone growth and fusion through one or more openings in the base plates. The bone growth promoting material can then be allowed to aid in intervertebral fusion of the adjacent vertebrae while the device stably supports the vertebrae with zero degrees of freedom of movement, or fewer if the device includes redundant constraints.

The above summary of the various embodiments of the invention is not intended to describe each illustrated embodiment or every implementation of the invention. This summary represents a simplified overview of certain aspects of the invention to facilitate a basic understanding of the invention.

BRIEF DESCRIPTION OF THE DRAWINGS

The invention may be more completely understood in consideration of the following detailed description of various embodiments of the invention in connection with the accompanying drawings, in which:

FIG. 1A is a rear view of an embodiment of an expandable intervertebral cage device according to an aspect of the present invention;

FIG. 1B is a side view of an embodiment of an expandable intervertebral cage device according to an aspect of the present invention;

FIG. 1C is a top view of an embodiment of an expandable intervertebral cage device according to an aspect of the present invention;

FIG. 3A is a perspective view of an embodiment of a first base plate according to an aspect of the present invention;

FIG. 3B is a perspective view of an embodiment of a second base plate according to an aspect of the present invention;

FIG. 3C is a side view of an embodiment of a base plate according to an aspect of the present invention;

FIG. 4 is a perspective view of an embodiment of an arm according to an aspect of the present invention;

FIG. 6 is a perspective view of an embodiment of a pin according to an aspect of the present invention;

FIG. 7 is an exploded view of an embodiment of an expandable intervertebral cage device according to an aspect of the present invention;

FIGS. 8A-B are side and perspective views an embodiment of an expandable intervertebral cage device according to an aspect of the present invention in a distracted state, wherein the nose portion is further distracted that the rear portion;

FIGS. 9A-B are side and perspective views an embodiment of an expandable intervertebral cage device according to an aspect of the present invention in a distracted state, wherein the rear portion is further distracted that the nose portion;

FIGS. 10A-B are side and perspective views of an embodiment of an expandable intervertebral cage device according to an aspect of the present invention in a distracted state, wherein the rear portion and nose portion are substantially equally distracted;

Figure 2:
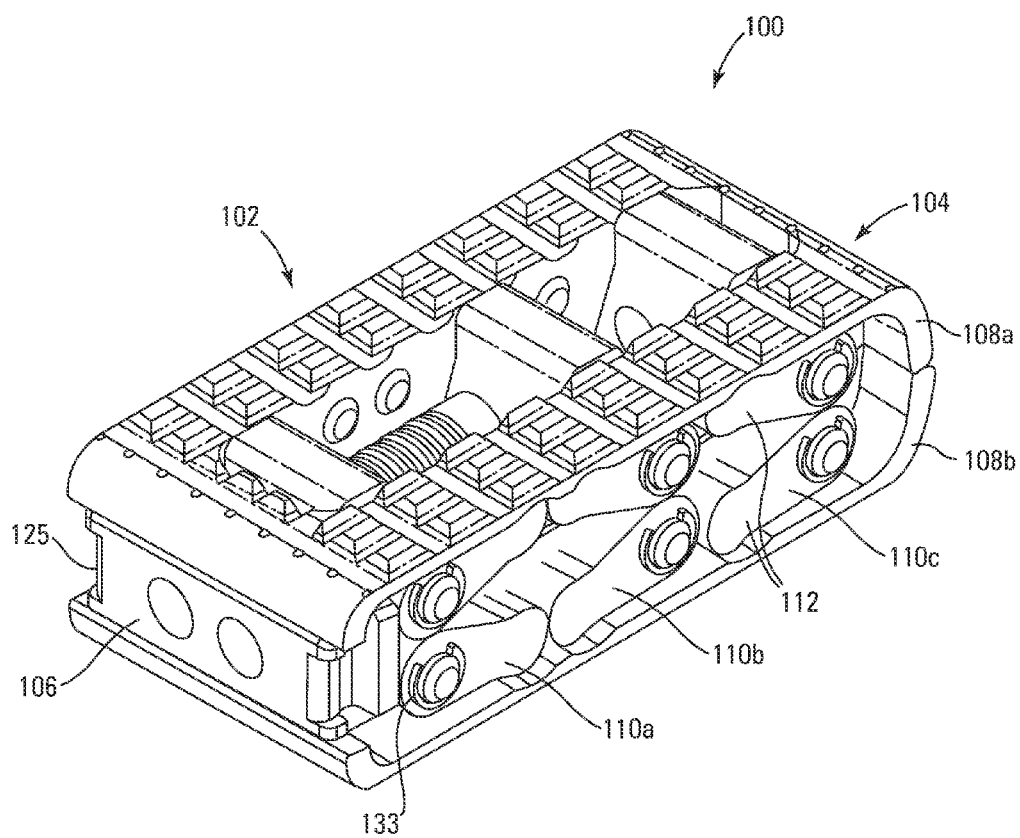
FIG. 2 is a perspective view of an embodiment of an expandable intervertebral cage device according to an aspect of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

In the following detailed description of the present invention, numerous specific details are set forth in order to provide a thorough understanding of the present invention. However, one skilled in the art will recognize that the present invention may be practiced without these specific details. In other instances, well-known methods, procedures, and components have not been described in detail so as to not unnecessarily obscure aspects of the present invention. U.S. Pat. No. 8,628,577, invented by the inventor of the present application, discloses a stable intervertebral body fusion and distraction device. This patent is hereby incorporated herein by reference in its entirety other than the summary of the invention, claims and any express definitions set forth therein.

Figure 12A:
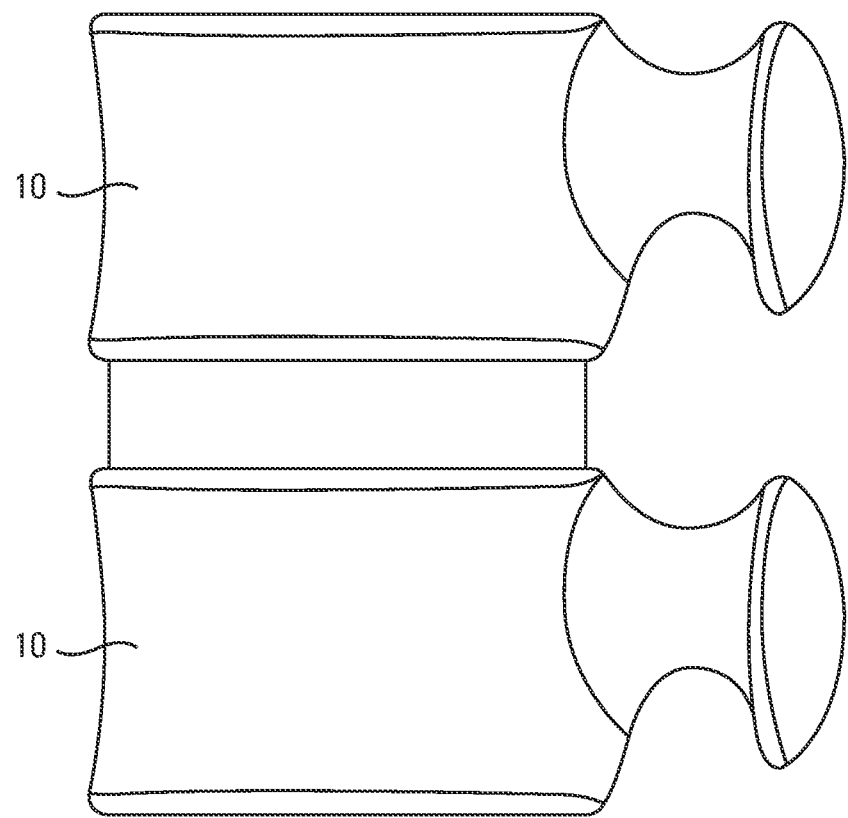
FIGS. 12A-12B are schematic representations of a pair of adjacent vertebral bodies.
Figure 12B:
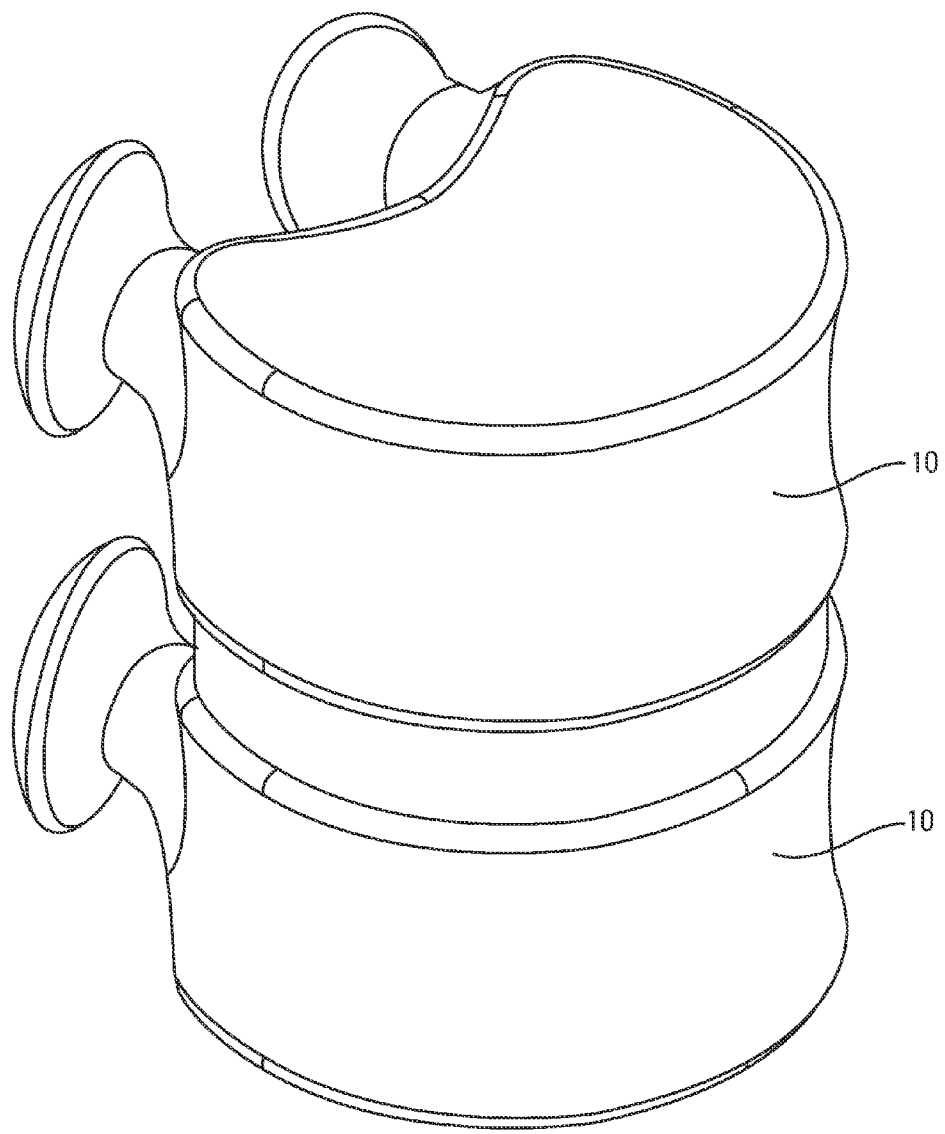

Referring to FIGS. 1A-1C and FIG. 2, there can be seen an expandable intervertebral cage device 100 according to an aspect of the present invention. Device 100 includes a device body 102. Device body 102 can include a nose portion 104, a rear portion 106, a pair of opposed base plates 108 having outer bearing surfaces 107, and a plurality of arm assemblies 110. As used throughout this disclosure, "bearing surface" refers to the outside surface of a base plate that interfaces with the endplate of a vertebra. Schematic representations of a pair of adjacent vertebral bodies 10 are depicted in FIGS. 12A-12B. Each arm assembly 110 can include a pair of opposed arms 112 hingedly attached to each other, with each opposing arm 112 hingedly attached to one of the base plates 108. In one embodiment, device 100 can include three arm assemblies 110a, 110b, and 110c, extending crosswise from first side 116 of device 100 to second side 118 of device 100. In one embodiment, opposing arms 112 of arm assemblies 100a, 110b, and 110c are pivotally coupled to a blocks 122a, 122b, and 122c with pins 114. Block 122a can be positioned nearest the rear portion 106, block 122c can be positioned nearest the nose portion 104, and block 122b can be positioned between blocks 122a and 122c.

Referring to FIGS. 3A-C, in one embodiment, base plates 108 can include a first, or top, base plate 108a, with a top bearing surface 107a configured to interface with an end plate of a superior vertebra of the intervertebral disc space, and a second, or bottom, base plate 108b having a bottom bearing surface 107b configured to interface with an end plate of an inferior vertebra of the intervertebral disc space. In one embodiment, each base plate 108 can include one or more openings 124 to facilitate bone growth through the device 100. Openings 124 promote vertebral fusion because bone can grow directly through the device 100. Although depicted as being generally rectangular, opening 124 can comprise any shape. Alternatively, a generally solid surface or a surface with multiple openings can be provided on each base plate 108.

Base plates 108 can have a rough surface or teeth 109 to create friction with the base plates of the vertebra to prevent accidental extrusion of the device 100 or to promote bone growth for successful fusion. Base plates 108 or other elements of the device can also in some embodiments be made compliant for exaggerated non-uniform distraction while maintaining the stability of the device 100. Nose portion 104 can be tapered to facilitate insertion of the device 100 into the disc space. Rear portion 106 can also be tapered. In one embodiment, base plate 108 can include a plurality of bores 105. Each bore 105 can be sized to accept a portion of opposing arm 112 to facilitate a hinged coupling.

In one embodiment, device 100 can have a total of twelve arms 112 (four arms for each arm assembly 110a, 110b, and 110c, with two arms of each assembly on each side of the device). In one embodiment, all of the arms 112 can be substantially identical. Referring to FIG. 4, each arm 112 can include a protrusion 113 sized to fit into one of the bores 105 of base plate 108 to facilitate a hinged coupling. In one embodiment, arms 112 can be welded to base plates to prevent failure. Each arm 112 can include a bore 115 sized to accept a pin 114 for coupling the arm 112 to a block 122.

Figure 5:
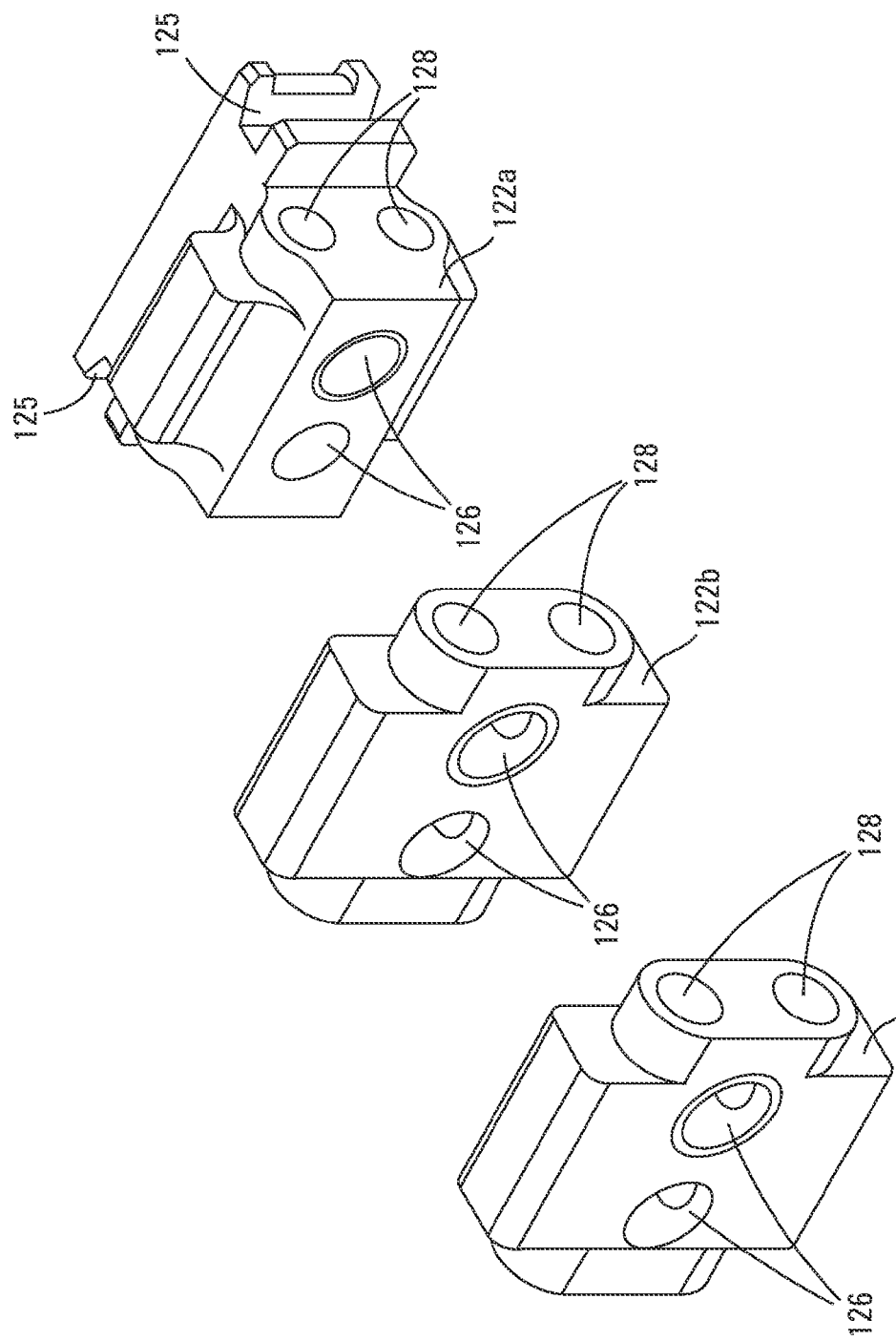
FIG. 5 is a perspective view of an embodiment of first, second and third blocks according to an aspect of the present invention.

In one embodiment, device can have a total of three blocks—a first or proximal block 122a, a second or central block 122b and a third or distal block 122c. Referring to FIG. 5, in one embodiment, central and distal blocks 122b and 122c can be substantially identical. Each block 122 can be defined by two side bores 128 sized to accept pin 114 for the purpose of coupling two arms 112 to block 122. In one embodiment, side bores 128 can be substantially parallel to one another. Each block 122 can also be defined by two longitudinal bores 126, each sized to accept an actuation member 120. In one embodiment, each longitudinal bore 126 can be threaded. In another embodiment, only one longitudinal bore 126 of each block 122 is threaded. In one embodiment, longitudinal bores 126 can be substantially parallel to one another. In one embodiment, longitudinal bores 126 can be orthogonal to side bores 128. Proximal block 122a can be adapted to attach to an insertion device for inserting device 100 into the disc space. In one embodiment, side slots 125 of proximal block 122a can be configured to receive portions of insertion device.

In one embodiment, device 100 can include a total of six pins 114. Referring to FIG. 6, each pin 114 can be substantially cylindrical in shape and have opposing ends 127 sized to fit into bore 115 of arms 112 on opposing sides 116, 118 of device 100. Pins can be sized to extend through side bore 128 of block 122 between opposing arms 112, for the purpose of pivotably coupling two arms 112 to a given block 122. In one embodiment, pin 114 can include notches 129. Notches 129 can be sized to allow clearance for actuation members 120 through longitudinal bores 126, thereby allowing each arm assembly 110 to be more compact. In one embodiment, pin 114 can include a slot 131 proximate each end 127 of pin 114 sized to accept a snap ring 133 (shown in FIG. 7) that sits outside of arms to lock pins in place. In one embodiment, a distal portion of one or more actuation members 120 can have a larger diameter than the remainder of actuation member. Longitudinal bores 126 would therefore be larger to accommodate this larger section of the screw.

Referring to FIG. 7, in one embodiment, device 100 can include a first actuation member 120a and a second actuation member 120b. In one embodiment, actuation members 120a and 120b can be substantially identical. In one embodiment, actuation member 120 can include a threaded portion 135 of a diameter sized to threadedly couple with longitudinal bore 126 of one or more blocks 122. Actuation member 120 can include a second non-threaded portion 136 having a smaller diameter than threaded portion 135. One end of actuation member 120 can be defined by a slot or socket 138 structured to receive a tool for driving actuation device 120. In one embodiment, socket 138 can be capable of receiving a hex key or Allen wrench, for example, for rotatably driving actuation device 120. In one embodiment, actuation member 120 can include a slot 137 proximate one end of actuation member 120 sized to accept snap ring 139 that can lock actuation members in axial position relative to blocks. Alternatively, snap ring 139 can be located at the proximal end of block 122c, which provides further stability to the screw and reduces the stress on the snap ring.

In one embodiment, first actuation member 120a can extend through first arm assembly 110a into second arm assembly 110a. For example, first actuation member 120a can be threadedly coupled to first arm assembly 110a and rotationally coupled to second arm assembly 110b. Second actuation member 120b can extend through second arm assembly 110a into third arm assembly 110c. For example, second actuation member 120a can be threadedly coupled to second arm assembly 110b and rotationally coupled to third arm assembly 110c.

As shown in FIGS. 8A-8B, in one embodiment, actuation of first actuation member 120a in a first direction drives blocks 122a and 122b closer together, which causes expansion of arm assemblies 110a and 110b and distraction of base plates 108. As shown in FIGS. 9A-9B, actuation of second actuation member 120*b* in a first direction drives blocks 122*b* and 122*c* closer together, which causes expansion of arm assemblies 110*a* and 110*b* and distraction of base plates 108.

First actuation member 120*a* and second actuation member 120*b* are capable of being actuated independently of each other. This independent actuation allows for angular orientation of the base plates 108 to be matched exactly to the unique alignment, or desired planar alignment, of adjacent vertebrae of a patient's spine. Examples of various possible angular orientations of base plates 108 in the distracted state can be seen at FIGS. 8A-10B. Such angulations can be done when the device is expanded within the disc space, enabling the device to go between lordotic and kyphotic angles while in the disc space so that the surgeon can adjust as needed to correct the deformity based on observations made during the procedure.

Conversely, actuation of first actuation member 120*a* in the opposite direction drives blocks 122*a* and 122*b* apart, thereby bringing base plates 108 closer together. Likewise, actuation of second actuation member 120*b* in the opposite direction drives blocks 122*b* and 122*c* apart, thereby bringing base plates 108 closer together. This back-drivability of the device 100 is helpful for sizing the device 100 and removing the device 100 if necessary, such as in the event of post-surgical infection, trauma, or failure to fuse.

Referring again to FIG. 7, non-threaded portion 136 of actuation member 120 and its respective rotational coupling to block 122 enable device 100 to allow for additional distraction due to in-vivo axial tension. For example, the rotational coupling can be constructed with sufficient clearance to allow block 122*b* to temporarily slide closer to 122*a*, or block 122*c* to temporarily slide closer to block 122*b*. However, having distracted slightly under tensile loading the device would return to the original height as compressive loading is returned. The parallelism would remain unchanged, while lordotic endplates may undergo a small angular displacement that would return to the set lordosis with the reapplication of the normal compressive loading. This extensibility of device 100 could offer great benefits to the fusion process as the endplates, which may be growing into the endplates of the vertebral bodies, would not be pulled away from the endplates by motion of the patient's spine, damaging early bone growth.

In another embodiment, in place of non-threaded portion 136 and snap ring 139, portions of the actuation member 120 can be reverse threaded to allow distraction without changing the position of the threaded members along the respective axes of the threaded members helping to keep the device from adversely interacting with the anatomy of the patient.

In various embodiments, device body 102 is shaped to be ergonomic. Device body 102 can have various shapes, such as, for example, rectangular or kidney-shaped. A kidney-shaped device body 102 maximizes contact between the device and the vertebral bodies because the base plates of vertebrae tend to be slightly concave. One or both ends of the device may also be tapered to facilitate insertion. This minimizes the amount of force needed to initially separate the vertebral bodies. In addition, the device may be convex along both its length and its width, or bi-convex. Device body can also be comprised of various materials. Such materials can include, for example, titanium, steel, PEEK, carbon fiber and cobalt chromium. The device can also be constructed in various sizes depending on the type of vertebra and size of patient with which it is being used, for example, specifically for an anterior lumbar interbody fusion, oblique or a lateral interbody fusion. In some embodiments, the threaded member 120 can be micro-machined or split along its length and reconnected using a bellows or flexible torque transmission device, to be able to operate through an angle that may be necessitated by the shape of the device.

In one embodiment, a locking mechanism can be utilized to prevent rotation of the threaded members to ensure the device remains in the distracted state. In one embodiment, the locking mechanism can be activated with the insertion device. In one embodiment, locking may be enhanced by tightening a threaded nut (not shown) against one or more of the blocks 122.

Figure 11:
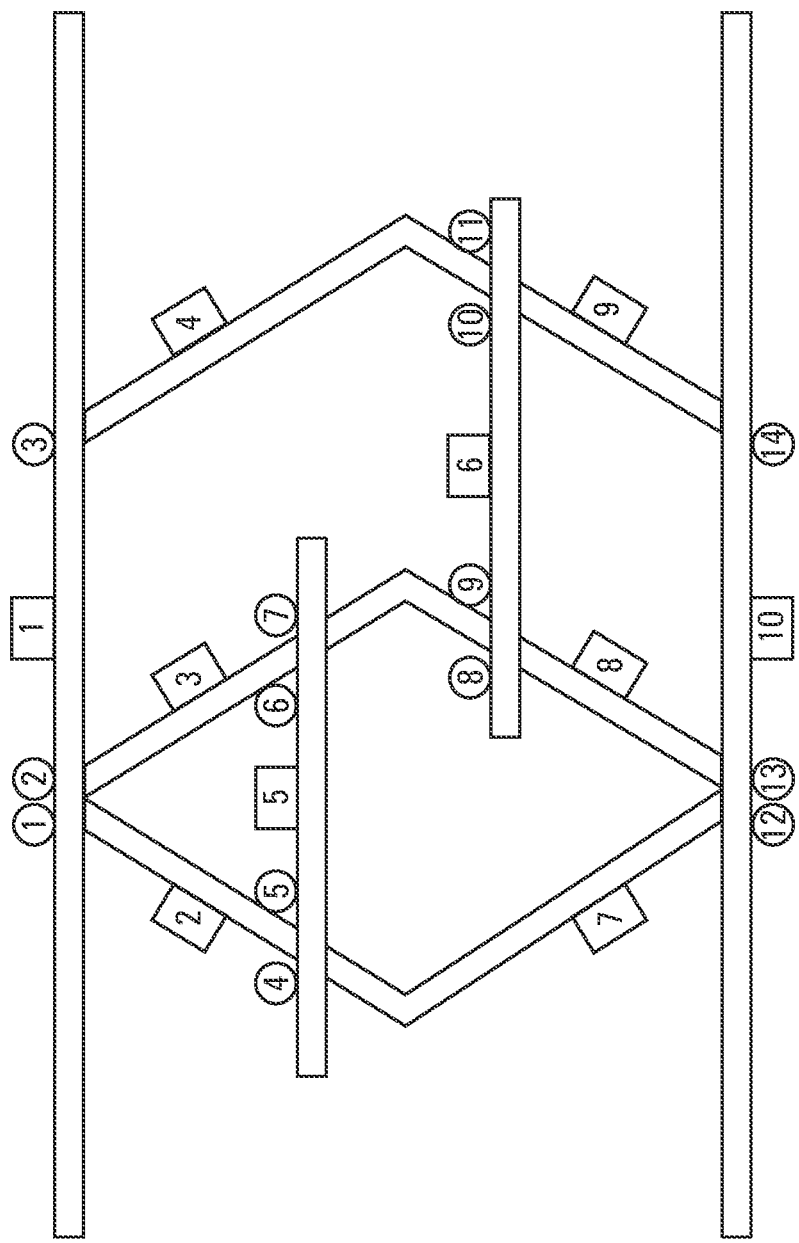
FIG. 11 is a simplified view of an embodiment of an expandable intervertebral cage device according to an aspect of the present invention.

As is demonstrated by a simplified form of device 100 shown in FIG. 11, device 100 can stably support the disc space because it has negative one degree of freedom once locked in the distracted position with actuation members 120 in place. From Gruebler's equation, the number of degrees of freedom=$3*(n-1)-2f$, where n is the number of links in the linkage and f is the number of one degree of freedom kinematic pairs in the linkage. As is shown in FIG. 11, the device 100 has 10 links and 14 kinematic pairs, so $3*(10-1)-2*14=-1$ degrees of freedom. The device is therefore actually over constrained (meaning that there are additional constraints beyond the minimum necessary to make it stable), and stable under loading conditions. This allows device 100 to stably support the disc space upon distraction. In some embodiments, a crush surface or compliant materials may be used in concert with structure to minimize hysteresis that may be present in the device and due to clearance in arm assemblies 112 necessary for overcoming the over-constraint in devices having fewer than zero degrees of freedom due to redundant constraints.

In operation, device 100 can be placed between adjacent vertebrae or vertebral bodies and used to distract the endplates of the adjacent vertebral bodies and subsequently serve as a fusion device. One or more insertion tools (not depicted) can be used to insert and distract device 100. Referring to FIGS. 1A-2, the device body 102 can be seen in its initial compressed configuration. In FIGS. 8A-10B, device body 102 is in various expanded configurations. The insertion tool can be connected to actuation members 120 with the proximal block 122*a* and first used to insert device 100 into a desired location. Device 100 can be inserted with tapered nose portion 104 first. One device 100 can be inserted, or, for additional support, two devices 100 can be inserted. Two devices 100, each sized to be inserted within one-half of the evacuated disc space, can be especially useful for treating larger patients in which the device may encounter higher loads. In another embodiment, three or more small devices can be inserted into the disc space in order to very accurately control the orientation and distance between the discs. Three or more distraction mechanisms may be positioned circumferentially between two circular endplates to result in very accurate control and orientation of the base plates. Such a device would resemble a hexapod.

To distract device 100, an insertion tool can be used to rotate actuation members 120 in a first direction. Actuation of threaded member 120*a* in a first direction drives blocks 122*a* and 122*b* closer together, which causes distraction of base plates 108. Likewise, actuation of threaded member 120*b* in a first direction drives blocks 122*b* and 122*a* closer together, which causes distraction of base plates 108. Actuation of threaded members 120*a* and 120*b* in the opposite direction respectively drives blocks 122*a* and 122*b* and blocks 122*b* and 122*c* apart, thereby bringing base plates 108 closer together.

Once base plates 108 are distracted to a desired degree, insertion tools can be disconnected from threaded members 120 and the device 100 can remain within the body. In one embodiment, a locking mechanism can be utilized to prevent rotation of the threaded members to ensure the device remains in the distracted state.

Once device is inserted and supporting the adjacent vertebral bodies, it can be utilized to promote vertebral fusion. Following distraction, a bone growth stimulant, such as autograft, bone morphogenic protein, or bone enhancing material, can be delivered into an open area defined within the device. In one embodiment, bone growth stimulant is delivered after insertion tools are disconnected. In another embodiment, bone growth stimulant is delivered through an open area between insertion tools. In a further embodiment, bone growth stimulant can be delivered through a hollow chamber within the insertion tools. Device is capable of supporting in-vivo loads during the 6 to 12 weeks that fusion occurs between the vertebral bodies. In one embodiment, openings 124 in base plates 108 promote and allow for bone growth into and through the device 100.

In some embodiments, when the device is implanted and in the process of being expanded, as blocks come closer together the blocks compress the bone graft or bone fusion material that can be inserted inside device to force the material out of the internal chamber of the device an in the adjacent vertebral end plates. This will enhance bone integration into the end plates. Some bone material will remain within the cage, which will integrate and fuse the center of the cage to the top and bottom of the end plates. In certain embodiments, the bone material can be injected into the device through one of the longitudinal holes in the proximal block of the device that does not have an actuation member therethrough. This could be done with the inserter device or separate extended syringe. In some embodiments, the top and bottom base plates of the device can be coated to enhance bone integration.

In an alternative embodiment, a pin can extend vertical through the device to stabilize the proximal end of the device. Such a device could be expanded utilizing only a distal set of arm assemblies and would provide only lordotic angles. Alternatively the pin could stabilize the distal end of the device, which could then be expanded with a single screw and one or more proximally located arm assemblies to provide kyphotic angles.

Although the various devices described herein are described as being brought from a compressed configuration to an expanded configuration by rotation of a threaded member, the devices can be distracted by any other type of actuation member. In some embodiments, mechanisms other than threaded members can be used to distract the device. Such mechanisms include, for example, a pop-rivet mechanism, a sardine key and ribbon, a tourniquet and wire, a saw blade/ratchet, a zip-tie-like mechanism, piezo-electric inch worm motors and shape changing materials such as a shape member alloy or a conducting polymer actuator. These alternative locking mechanisms could be designed to make the device behave as if it were locked with a threaded member, preventing the device from being compressed as well as extended, or these mechanisms could afford the device the capability to ratchet upwards post implantation if such action would benefit the patient or provide additional therapy.

Various embodiments of implantation procedures for the disclosed embodiments of expandable intervertebral cage devices may be as follows:

Lumbar: A lumbar implant can be 8 mm in height, expandable to 14 mm in height, with a length of 25-30 mm and a width of 10-12 mm. The implant can be inserted through a minimally invasive tubular port that goes through the muscle of the lumbar spine and into the lumbar disc space. Prior to inserting the implant, the lumbar disc should be completely removed. Other embodiments for the lumbar spine include larger sizes for anterior, posterior, transforaminal, oblique lateral, and lateral interbody fusions.

Cervical: A cervical implant can be 6 mm in height, expandable to 10 mm in height, with a length of 10 mm and a width of 6 mm. The implant can be inserted after anterior cervical surgical exposure. The cervical disc should be completely removed prior to insertion of the implant.

Various embodiments of systems, devices, and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

What is claimed is:

1. An expandable intervertebral cage device adapted to be implanted into an intervertebral disc space in a patient's body, comprising:
    a first base plate having a first outer bearing surface configured to interface with a first vertebra of the intervertebral disc space;
    a second base plate having a second outer bearing surface configured to interface with a second vertebra of the intervertebral disc space;
    a proximal arm assembly hingedly connected to the first base plate and the second base plate;
    a central arm assembly hingedly connected to the first base plate and the second base plate;
    a distal arm assembly hingedly connected to the first base plate and the second base plate;
    a first actuation member extending through the proximal arm assembly and into the central arm assembly and not into the distal arm assembly, the first actuation member configured such that actuation of the first actuation member causes expansion of the proximal arm assembly and central arm assembly such that the first bearing surface and second bearing surface move away from each other into a distracted position, wherein rotation of the first actuation member pulls the central arm assembly towards the proximal arm assembly and rotation of the first actuation member in a second direction pushes the central arm assembly away from the proximal arm assembly;
    a second actuation member extending through the central arm assembly and into the distal arm assembly and not into the proximal arm assembly, the second actuation member configured such that actuation of the second actuation member causes expansion of the central arm assembly and distal arm assembly such that the first bearing surface and second bearing surface move away from each other into a distracted position, wherein rotation of the second actuation member pulls the distal arm assembly towards the central arm assembly and rotation of the second actuation member in a second direction pushes the distal arm assembly away from the central arm assembly; and
    wherein the first actuation member and the second actuation member are capable of being actuated independently of each other.

2. The device of claim 1, wherein each arm assembly comprises a block and a pair of opposing arms.

3. The device of claim 2, wherein each opposing arm comprises two structural members.

4. The device of claim 3, wherein two opposing structural members of opposing arms are pivotably coupled to the block by a common pin that extends through the block between the structural members.

5. The device of claim 1, wherein the top base plate and bottom base plate each have an opening defined therein configured to allow bone growth into an open space defined by the device.

6. The device of claim 1, wherein the proximal arm assembly includes a threaded portion through which the first actuation member is threadedly coupled and the central arm assembly includes a non-threaded rotational coupling to which the first actuation member is non-threadedly rotationally coupled and wherein the central arm assembly includes a threaded portion through which the second actuation member is threadedly coupled and the distal arm assembly includes a non-threaded rotational coupling to which the second actuation member is non-threadedly rotationally coupled.

7. An expandable intervertebral cage device adapted to be implanted into an intervertebral disc space in a patient's body, comprising:
   a top base plate having a top bearing surface configured to interface with an end plate of a superior vertebra of the intervertebral disc space;
   a bottom base plate having a bottom bearing surface configured to interface with an end plate of an inferior vertebra of the intervertebral disc space;
   proximal, central and distal arm assemblies, wherein each arm assembly is connected to the top base plate and the bottom base plate and each arm assembly comprises a block and a pair of opposing arms;
   a first actuation member extending through the block of the proximal arm assembly and into the block of the central arm assembly, the first actuation member configured such that actuation of the first actuation member causes expansion of the proximal arm assembly and central arm assembly such that the top bearing surface and bottom bearing surface move away from each other into a distracted position, wherein rotation of the first actuation member pulls the central arm assembly towards the proximal arm assembly and rotation of the first actuation member in a second direction pushes the central arm assembly away from the proximal arm assembly;
   a second actuation member extending through the block of the central arm assembly and into the block of the distal arm assembly, the second actuation member configured such that actuation of the second actuation member causes expansion of the central arm assembly and distal arm assembly such that the top bearing surface and bottom bearing surface move away from each other into a distracted position, wherein rotation of the second actuation member pulls the distal arm assembly towards the central arm assembly and rotation of the actuation member in a second direction pushes the distal arm assembly away from the central arm assembly; and
   wherein the first actuation member and the second actuation member are capable of being actuated independently of each other such that the central arm assembly can be pulled towards the proximal arm assembly without directly moving the distal arm assembly with the first actuation member and the distal arm assembly can be pulled towards the central arm assembly without directly moving the proximal arm assembly with the second actuation member.

8. The device of claim 7, wherein each opposing arm comprises two structural members.

9. The device of claim 8, wherein two opposing structural members of opposing arms are pivotably coupled to the block by a common pin that extends through the block between the structural members.

10. The device of claim 7, wherein the top base plate and bottom base plate each have an opening defined therein configured to allow bone growth into an open space defined by the device.

11. The device of claim 7, wherein the block of the proximal arm assembly includes a threaded portion through which the first actuation member is threadedly coupled and the block of the distal arm assembly includes a non-threaded rotation coupling to which the actuation member is non-threadedly rotationally coupled and wherein the block of the central arm assembly includes a threaded portion through which the second actuation member is threadedly coupled and the block of the distal arm assembly includes a non-threaded rotation coupling to which the second actuation member is non-threadedly rotationally coupled.

12. A method comprising:
   providing an expandable intervertebral cage device, comprising:
      a first base plate having a first outer bearing surface;
      a second base plate having a second outer bearing surface;
      a proximal arm assembly hingedly connected to the first base plate and the second base plate;
      a central arm assembly hingedly connected to the first base plate and the second base plate;
      a distal arm assembly hingedly connected to the first base plate and the second base plate;
      a first actuation member extending through the proximal arm assembly and into the central arm assembly and not into the distal arm assembly, the first actuation member configured such that actuation of the first actuation member causes expansion of the proximal arm assembly and central arm assembly such that the first bearing surface and second bearing surface move away from each other into a distracted position, wherein rotation of the first actuation member pulls the central arm assembly towards the proximal arm assembly and rotation of the first actuation member in a second direction pushes the central arm assembly away from the proximal arm assembly;
      a second actuation member extending through the central arm assembly and into the distal arm assembly and not into the proximal arm assembly, the second actuation member configured such that actuation of the second actuation member causes expansion of the central arm assembly and distal arm assembly such that the first bearing surface and second bearing surface move away from each other into a distracted position, wherein rotation of the second actuation member pulls the distal arm assembly towards the central arm assembly and rotation of the second actuation member in a second direction pushes the distal arm assembly away from the central arm assembly; and
      wherein the first actuation member and the second actuation member are capable of being actuated independently of each other;
   providing instructions for performing an intervertebral body fusion and distraction procedure with the expandable intervertebral cage device, the instructions comprising:

inserting the expandable intervertebral cage device into an intervertebral disc space of a patient defined between adjacent vertebrae such that the top bearing surface interfaces with an end plate of a superior vertebra of the intervertebral disc space and the bottom bearing surface interfaces with an end plate of an inferior vertebra of the intervertebral disc space;

expanding the device within the intervertebral disc space into an expanded configuration by actuating one or both of the first actuation member and the second actuation member; and leaving the device within the intervertebral disc space following the insertion procedure.

13. The method of claim 12, wherein expanding the device includes actuating one of the first actuation member and the second actuation member more than the other such that the base plates of the device are positioned at a non-parallel angle within the disc space.

14. The method of claim 13, wherein the first actuation member is actuated more than the second actuation member such that the base plates angle inwardly from proximal to distal.

15. The method of claim 13, wherein the second actuation member is actuated more than the first actuation member such that the base plates angle outwardly from distal to proximal.

16. The method of claim 12, wherein the instructions further comprise inserting a bone growth material into an open area within the device prior to expanding the device.

17. The method of claim 16, wherein inserting a bone growth material includes inserting the bone growth material through an opening defined through the proximal arm assembly.

18. The method of claim 16, wherein expanding the device includes forcing a portion of the bone growth material out of the open area within the device and into contact with the end plates of the intervertebral disc space.

* * * * *